United States Patent
Sparks et al.

(10) Patent No.: US 7,437,912 B2
(45) Date of Patent: Oct. 21, 2008

(54) DEVICE AND METHOD FOR SENSING RHEOLOGICAL PROPERTIES OF A FLUID

(75) Inventors: Douglas Ray Sparks, Whitmore Lake, MI (US); Nader Najafi, Ann Arbor, MI (US)

(73) Assignee: Integrated Sensing Systems, Inc., Ypsilanti, MI (US)

( * ) Notice: Subject to any disclaimer, the term of this patent is extended or adjusted under 35 U.S.C. 154(b) by 89 days.

(21) Appl. No.: 11/184,620

(22) Filed: Jul. 19, 2005

(65) Prior Publication Data

US 2006/0010964 A1    Jan. 19, 2006

Related U.S. Application Data

(60) Provisional application No. 60/588,669, filed on Jul. 19, 2004.

(51) Int. Cl.
*G01N 11/00* (2006.01)
*G01N 11/08* (2006.01)

(52) U.S. Cl. .................... 73/54.01; 73/53.07; 73/54.02; 73/54.09

(58) Field of Classification Search ............. 73/53.01, 73/53.07, 53.05, 54.41, 861.355, 54.01, 54.02, 73/54.23, 54.09
See application file for complete search history.

(56) References Cited

U.S. PATENT DOCUMENTS

| | | | | | |
|---|---|---|---|---|---|
| 3,903,731 | A | * | 9/1975 | Sieben | 73/54.24 |
| 4,627,272 | A | * | 12/1986 | Wright | 73/54.23 |
| 4,909,081 | A | * | 3/1990 | Kulczyk et al. | 73/597 |
| 5,315,863 | A | * | 5/1994 | Cowper | 73/54.09 |
| 5,754,055 | A | * | 5/1998 | McAdoo et al. | 324/636 |
| 6,378,357 | B1 | * | 4/2002 | Han et al. | 73/54.41 |
| 6,412,337 | B1 | * | 7/2002 | Arzate et al. | 73/54.09 |
| 6,477,901 | B1 | * | 11/2002 | Tadigadapa et al. | 73/861.352 |
| 6,647,778 | B2 | * | 11/2003 | Sparks | 73/204.26 |
| 7,059,176 | B2 | * | 6/2006 | Sparks | 73/54.41 |
| 2003/0020463 | A1 | * | 1/2003 | Carlson et al. | 324/204 |
| 2003/0066341 | A1 | * | 4/2003 | Shin et al. | 73/54.07 |
| 2004/0255648 | A1 | * | 12/2004 | Sparks | 73/54.41 |
| 2006/0218996 | A1 | * | 10/2006 | Matsiev et al. | 73/64.53 |

* cited by examiner

*Primary Examiner*—Hezron E. Williams
*Assistant Examiner*—Tamiko D Bellamy
(74) *Attorney, Agent, or Firm*—Hartman & Hartman, P.C.; Gary M. Hartman; Domenica N. S. Hartman (57) ABSTRACT

A method and device for assessing rheological properties of a fluid, including lubricity and viscosity. The invention utilizes a tube into which the fluid is introduced, and relies on tracking the movement of the fluid through the tube either alone or with one or more particles intentionally introduced into the fluid to assess the rheological properties of the fluid. The method and device generally entail flowing the fluid and the optional suspended particle through a passage within the tube, and assessing a rheological property of the fluid within the tube by tracking the movement of the fluid and/or particle through the portion relative to the flow of the fluid through the portion.

21 Claims, 6 Drawing Sheets

DEVICE AND METHOD FOR SENSING RHEOLOGICAL PROPERTIES OF A FLUID

CROSS REFERENCE TO RELATED APPLICATIONS

This application claims the benefit of U.S. Provisional Application No. 60/588,669, filed Jul. 19, 2004.

STATEMENT REGARDING FEDERALLY SPONSORED RESEARCH

This invention was made with Government support under Agreement No. W56HZV-05-C-0126, awarded by the U.S. Department of Defense. The Government has certain rights in the invention.

BACKGROUND OF THE INVENTION

The present invention generally relates to devices and methods for measuring properties of fluids. More particularly, this invention relates to a sensing device equipped with a tube through which a fluid flows for sensing lubricity, viscosity, and other rheological properties of the fluid.

Viscosity and lubricity are important fluid parameters for a variety of fluids, including fuels, lubricants, adhesives, paints, oils, tars, electrophoresis gels, syrups, etc. For example viscosity, which is the internal resistance to flow exhibited by a fluid, is a key fluid parameter for lubricants such as automotive engine oils, whose viscosities change over time to the detriment of the components they lubricate. While oil quality sensors based on measuring the dielectric constant or electrical resistance of a lubricant have been developed and are commercially available, viscosity provides a better indication of the condition of an oil (and other lubricants) and when the oil should be replaced. Lubricity, or the coefficient of friction of a fluid, is often employed to characterize lubricants, fuels, diesel fuel additives, bearings, and load bearing surfaces. As with viscosity, the lubricity of fuels and lubricants often changes over time, such as from contamination from water and particulate matter. Consequently, there has been efforts to develop viscosity and lubricity sensors for fuel and lubricating system applications, including engine oil and fuel systems. For example, lubricity has been measured using slipping disks, bearings, shafts, and balls, which typically involve a long testing process requiring a relatively large amount of sample fluid. Techniques developed to measure viscosity have used capillary force, moving paddles, blades, vibrating tuning forks, and hollow tubes or cantilevers immersed in a fluid. More recently, rheometers and viscometers have been developed with a vibrating micromachined silicon cantilever immersed in the fluid of interest, with the resultant damping of the cantilever vibration being used to indicate viscosity.

Viscosity measuring techniques that rely on a vibrating structure require that the vibrating structure be inserted into the fluid being tested so that the fluid surrounds the structure. In contrast, commonly-assigned U.S. Pat. No. 6,647,778 to Sparks discloses a sensing device capable of sensing the viscosity of a fluid flowing through a microelectromechanical system (MEMS). Sparks' sensing device is used in combination with a micromachined resonating tube, preferably of the type disclosed in commonly-assigned U.S. Pat. No. 6,477,901 to Tadigadapa et al. and adapted for resonant sensing of mass flow and density of a fluid flowing through the tube. One embodiment of Sparks' sensing device incorporates second and third micromachined tubes having bridge portions adapted to deflect in response to a pressure change of the fluid flowing therethrough. Sparks ascertains the viscosity of the fluid flowing through the tubes by comparing the pressures of the fluid within the second and third tubes.

U.S. Pat. No. 7,059,176 to Sparks also discloses a method and device for assessing the viscosity of a fluid. Similar to U.S. Pat. No. 6,647,778 to Sparks, U.S. Pat. No. 7,059,176 utilizes a vibrating tube into which the fluid is introduced, but differs by sensing the influence that the fluid has on the vibrational movement of the tube to assess the viscosity of the fluid. More particularly, U.S. Pat. No. 7,059,176 entails introducing a fluid of interest into a passage within a freestanding portion of a tube, vibrating the freestanding portion of the tube at or near a resonant frequency thereof, sensing movement of the freestanding portion of the tube, and then assessing the viscosity of the fluid by ascertaining the damping effect the fluid has on the vibrational movement of the freestanding portion at or near the resonant frequency. The damping effect can be ascertained in reference to, for example, the quality (Q) factor or peak amplitude of the freestanding portion at the resonant frequency, or an amplitude-versus-.frequency plot of the freestanding portion in the vicinity of the resonant frequency.

Notwithstanding the above advancements, there is an ongoing need for techniques by which viscosity and lubricity can be measured, particularly more quickly and using smaller sample sizes than possible with existing lubricity measurement techniques.

BRIEF SUMMARY OF THE INVENTION

The present invention provides a method and device for assessing rheological properties of a fluid, including lubricity and viscosity. The invention utilizes a tube into which the fluid is introduced, and relies on tracking the movement of the fluid through the tube, either alone or with particles intentionally introduced into the fluid, to assess the Theological properties of the fluid.

According to the method of the invention, the fluid and optionally at least one solid particle suspended in the fluid is flowed through a passage within a portion of a tube, and a Theological property of the fluid within the tube is assessed by tracking movement of at least one of the fluid and the particle through the portion. For example, if the particle is suspended in the fluid, the assessing step comprises tracking the movement of the particle through the portion relative to the flow of the fluid through the portion, such as by a technique chosen from the group consisting of optical, infrared, ultrasonic, electrical, magnetic, and resonance sensing techniques. If the particle is not suspended in the fluid, movement of the fluid through the freestanding portion can be tracked by vibrating a freestanding portion of the tube at or near a resonant frequency thereof and monitoring changes in at least one of the signal peak gain and resonant frequency of the freestanding portion relative to time.

The sensing device of this invention comprises a tube supported by a substrate and comprising a fluid inlet, a fluid outlet, and a portion between the fluid inlet and the fluid outlet so as to define a continuous passage through the tube, optionally at least one solid particle in the fluid and flowing through the passage, and means for assessing a rheological property of the fluid within the tube by tracking movement of at least one of the fluid and the particle through the portion.

According to the invention, the viscosity and lubricity of a fluid can be assessed by observing the movement of a fluid through a resonating tube, and by observing the movement (or lack thereof) of particle(s) suspended in a fluid flowing through a tube portion and the influence that the particle or particles have on the fluid, such as the density, flow rate, pressure drop, etc., of the fluid. Various sensing techniques can be employed to sense the presence and movement of the particles through the tube portion and alter the behavior of the particles in order to enhance the sensitivity of the device to the Theological properties of the fluid within the tube. Advantageously, the device can be fabricated from a variety of materials using micromachining processes, enabling miniaturization of the device.

Other objects and advantages of this invention will be better appreciated from the following detailed description.

DETAILED DESCRIPTION OF THE INVENTION

Figure 1:
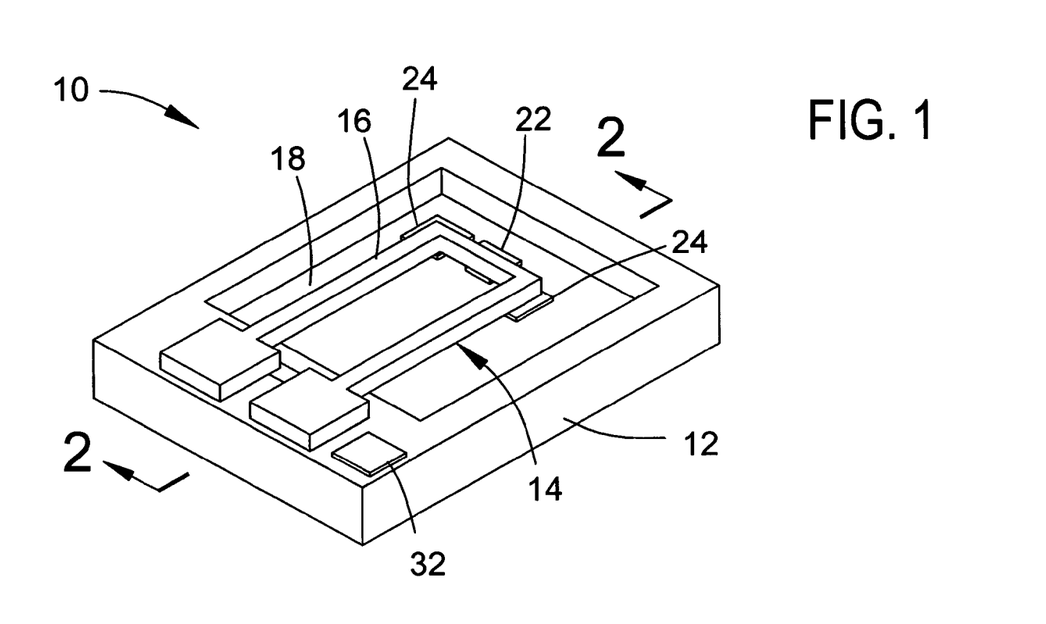
FIGS. 1 and 2 are perspective and cross-sectional views, respectively, of a sensing device with a resonating micromachined tube through which a fluid of interest flows in accordance with an embodiment of this invention.
Figure 2:
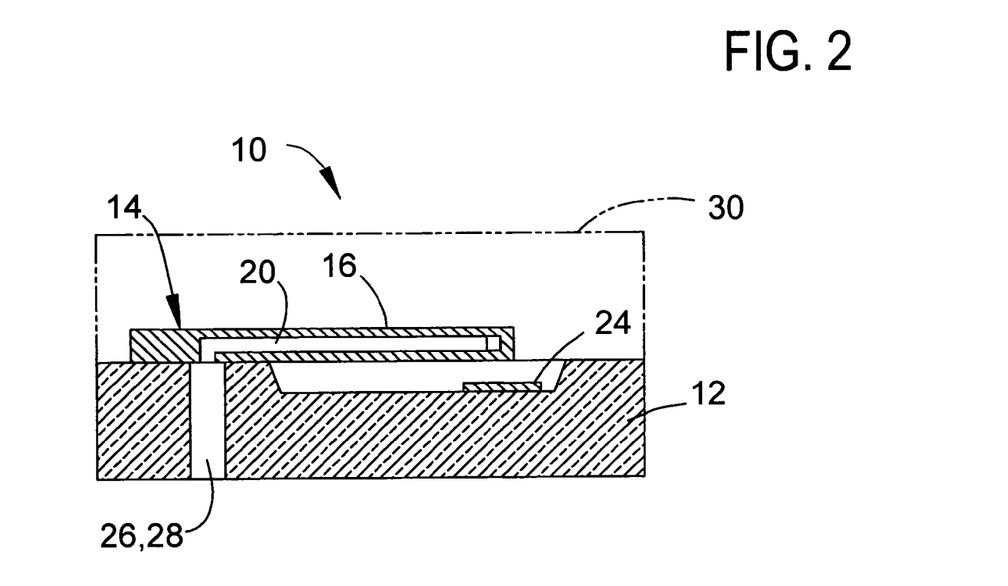

FIGS. 1 and 2 represent a viscosity sensing device 10 suitable for use in various embodiments of the present invention. The device 10, which may be termed a rheometer, is represented as being fabricated on a substrate 12, which can be formed of silicon or another semiconductor material, quartz, glass, ceramic, metal, or a composite material. A tube 14 is supported by the substrate 12 so as to have a freestanding portion 16 suspended above a surface 18 of the substrate 12, depicted in FIGS. 1 and 2 as being defined by a recess in the substrate 12. The freestanding portion 16 of the tube 14 is generally U-shaped, though other shapes—both simpler and more complex—are within the scope of this invention. The tube 14 defines a passage 20 through which a fluid can flow. Fluid is able to enter the device 10 through a fluid inlet 26 and exits the tube 14 through a fluid outlet 28 (one of which can be seen in FIG. 2) etched or otherwise formed in a surface of the substrate 12 opposite the tube 14.

According to a preferred aspect of the invention, the tube 14 is micromachined from silicon or another semiconductor material, quartz, glass, ceramic, metal or composite material. As used herein, micromachining is a technique for forming very small elements by bulk etching a substrate (e.g., a silicon wafer), or by surface thin-film etching, the latter of which generally involves depositing a thin film (e.g., polysilicon or metal) on a sacrificial layer (e.g., oxide layer) on a substrate surface and then selectively removing portions of the sacrificial layer to free the deposited thin film. The tube 14 can either be fabricated entirely from layers of the chosen materials deposited on the substrate 12, or fabricated in part by etching the substrate 12. The shape and size of the tube 14 can be chosen to provide an adequate flow capacity for the fluid and to have suitable vibration parameters for the intended fluids to be evaluated with the device 10. Because micromachining technologies are employed to fabricate the tube 14, the size of the tube 14 can be extremely small, such as lengths of about 0.5 mm and cross-sectional areas of about 250 $\mu m^2$, with smaller and larger tubes also being within the scope of this invention. Particularly suitable configurations and processes for fabricating resonant mass flow and density sensors using micromachining techniques are disclosed in commonly-assigned U.S. Pat. No. 6,477,901 to Tadigadapa et al., incorporated herein by reference, which uses wafer bonding and silicon etching techniques to produce a suspended silicon tube on a wafer.

According to Tadigadapa et al., micromachined tubes of the type shown in FIGS. 1 and 2 can be vibrated at or near resonance to determine the mass flow rate and density of a fluid flowing through the tube using Coriolis force principles. In the embodiments shown in FIGS. 1 through 7 and 9, the present invention also makes use of Coriolis force principles, though not solely for determining mass flow rate and density but also for the purpose of ascertaining the viscosity, lubricity, or other rheological property of a fluid flowing through the tube 14. As in Tadigadapa et al., the freestanding portion 16 is vibrated in a direction perpendicular to the surface 18 of the substrate 12, preferably at or near its resonant frequency. During half of the vibration cycle in which the tube 14 moves upward, the freestanding portion 16 has upward momentum as the fluid travels around the tube bends, and the fluid flowing out of the freestanding portion 16 resists having its vertical motion decreased by pushing up on that part of the freestanding portion 16 nearest the fluid outlet 28. The resulting force causes the freestanding portion 16 of the tube 14 to twist. As the tube 14 moves downward during the second half of its vibration cycle, the freestanding portion 16 twists in the opposite direction. This twisting characteristic is referred to as the Coriolis effect, and the degree to which the freestanding portion 16 of the tube 14 deflects during a vibration cycle as a result of the Coriolis effect can be correlated to the mass flow rate of the fluid flowing through the tube 14, while the density of the fluid is proportional to the frequency of vibration at resonance.

The resonant frequency of the tube 14 is controlled by its mechanical design (shape, size, construction and materials). Resonant frequencies will generally be in the range of about 1 kHz to about 100 kHz for tubes of the type fabricating in accordance with Tadigadapa et al. The amplitude of vibration is preferably adjusted through means used to vibrate the tube 14. As shown in FIGS. 1 and 2, a drive electrode 22 is located beneath the tube 14 on the surface 18 of the substrate 12. As depicted in FIGS. 1 and 2, the tube 14 is formed of an electrically-conductive material, such as doped silicon, and can therefore serve as an electrode that can be capacitively coupled to the drive electrode 22, enabling the electrode 22 to electrostatically drive the tube 14. However, it is foreseeable that the tube 14 could be formed of a nonconductive material, and a separate electrode formed on the tube 14 opposite the electrode 22 for vibrating the tube 14 electrostatically. An alternative driving technique is to provide a piezoelectric element on an upper surface of the tube 14 to generate alternating forces in the plane of the tube 14 that flex the freestanding portion 16 of the tube 14 in directions normal to the plane of the tube 14. Other alternatives are to drive the freestanding portion 16 of the tube 14 magnetically, thermally, piezoresistively, thermally, optically, or by another actuation technique. Also shown in FIGS. 1 and 2 are sensing electrodes 24 for providing feedback to the drive electrode 22 to enable the vibration frequency to be controlled with appropriate circuitry (not shown) while also sensing the deflection of the tube 14 relative to the substrate 12. The sensing electrodes 24 can sense the tube 14 capacitively, electrostatically, magnetically, piezoelectrically, piezoresistively, thermally, optically, or in any other suitable manner capable of sensing the proximity or motion of the tube 14.

In FIG. 2, the sensing device 10 is shown enclosed by a cap 30 to form a sensing package. The cap 30 allows for vacuum packaging that reduces air damping of the tube vibration. A variety of package and wafer-level methods exist to vacuum package devices. These include solder or weld hermetic packages, and wafer bonding using glass frit, solder, eutectic alloy, adhesive, and anodic bonding. A preferred material for the cap 30 is silicon, allowing silicon-to-silicon bonding techniques to be used, though it is foreseeable that a variety of other materials could be used for the cap 30, including metals and glass materials, that latter including borosilicate glass (e.g., Pyrex). Input and output signals to the device 10 are made through bond pads 32 (only one of which is shown) outside the cap 30. Since metal runners are used to transmit the electrical signals, and the capacitive signals produced by the tube 14 are relatively small, wafer to wafer bonding methods are preferred. Therefore, in the preferred embodiment of this invention, the bond between the cap 30 and the substrate 12 is hermetic, and the enclosure formed by the substrate 12 and cap 30 is evacuated to enable the tube 14 to be driven efficiently at high quality (Q) values without damping. In such an embodiment, a getter material is preferably placed in the enclosure to assist in reducing and maintaining a low cavity pressure. As an alternative to a hermetically sealed package, the tube 14 could be enclosed such that a vacuum can be drawn when desired through the use of a pump.

Figure 3:
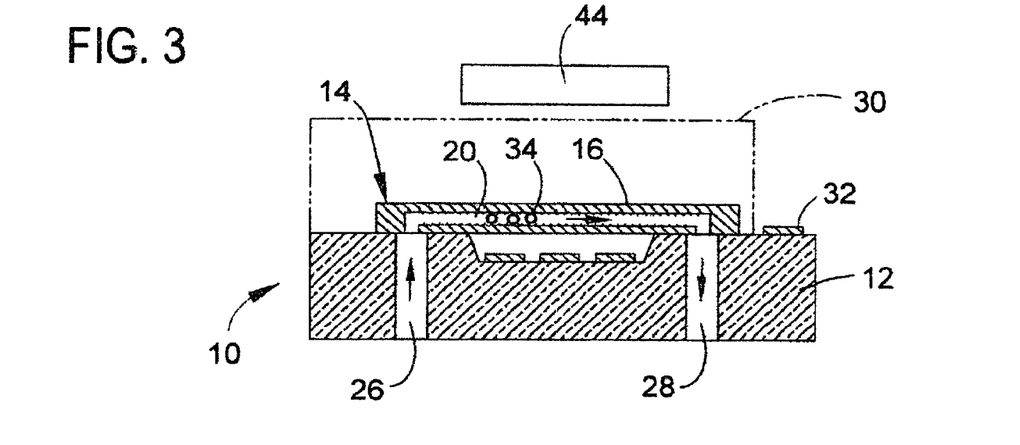
FIG. 3 is a cross-sectional view of the sensing device of FIG. 1 modified to magnetically alter the movement of particles being carried by a fluid flowing through the micromachined tube in accordance with further embodiments of this invention.

According to one approach of the invention, a micromachined resonating tube capable of sensing mass flow rate and density in accordance with Tadigadapa et al. is sufficiently sensitive to exhibit detectible changes in the resonant frequency of the tube when one or more particles of sufficient density and/or suitable material are present in the fluid flowing through the tube. With this capability, the viscosity or lubricity of a fluid within the micromachined resonating tube 14 can be ascertained by observing the effect that such particles have on the flow of the fluid and/or the time required for the particle(s) to travel through the tube 14 relative to the flow rate of the fluid. As represented in FIG. 3 (which is a section along, the extent of the tube 14), particles 34 such as microbeads are represented as having been intentionally added to the fluid so as to flow with the fluid through the tube passage 20 within the freestanding portion 16 of the tube 14. A suitable size for the particles 34 is a diameter of about one to one hundred micrometers, though larger and smaller particles 34 are also within the scope of this invention. While multiple particles 34 are represented in FIG. 3, it is foreseeable that a single particle 34 relatively large in relation to the passage 20 could be used. The functional intent of the particles 34 is to interact with the fluid and/or the walls of the passage 20 in a manner that enables rheological properties such as viscosity and lubricity of the fluid to be detected. For example, interaction of the particles 34 with the fluid that impedes the flow of the fluid through the tube 14 can be proportionally correlated to the viscosity of the fluid, arid interactions between particles 34 and between the particles 34 and the walls of the passage 20 that impede the movement of the particles 34 through the tube 14 can be proportionally correlated to the lubricity of the fluid. Therefore, by using a fixed pressure or flow rate through the freestanding portion 16 and tracking the flow of the fluid through the tube 14 and/or the motion of the particles 34 within the tube 14, the lubricity and/or viscosity of the fluid can be determined.

Figure 5:
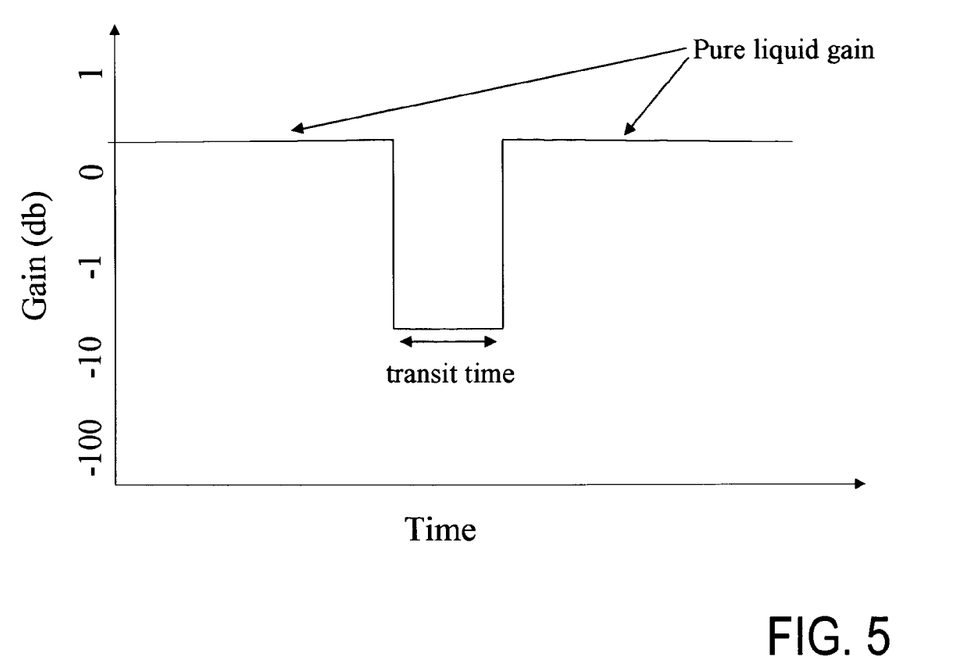
FIGS. 5 and 6 are graphs representing two modes for sensing the presence and transit time of a particle flowing through the sensing device of FIGS. 1 through 4 in accordance with this invention.
Figure 6:
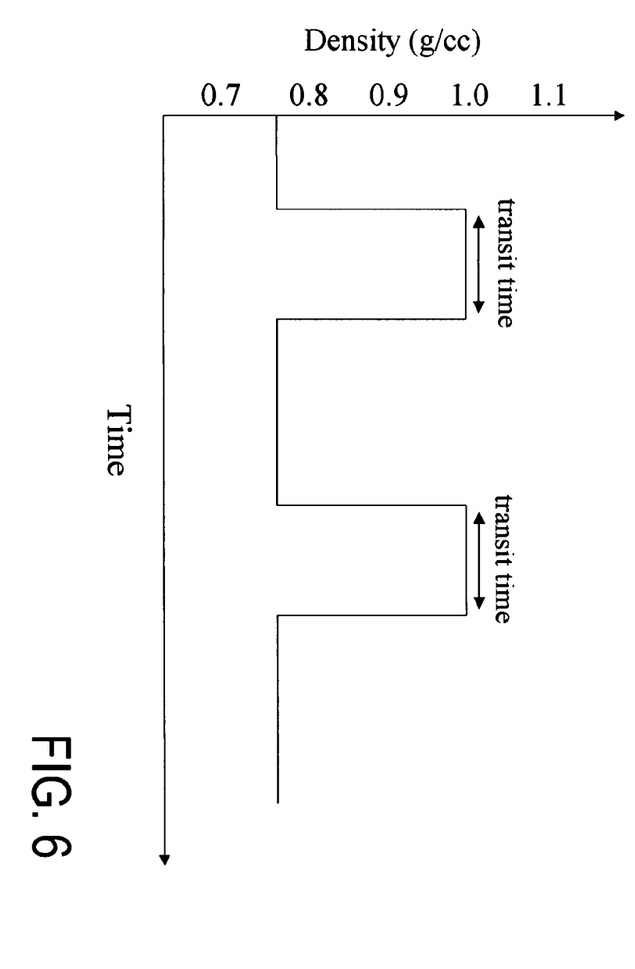

In the embodiment of FIG. 3, in which the resonant frequency of the freestanding portion 16 of the tube 14 is known to correspond to the density of the fluid within the freestanding portion 16, the use of particles 34 with densities different than (e.g., greater than) the fluid enables the presence of the particles 34 within the freestanding portion 16 to be detected by sensing a change in the resonant frequency of the freestanding portion 16 caused by the particles 34 entering (and leaving) the vibrating freestanding portion 16 of the tube 14. The time duration that the particles 34 are present in the freestanding portion 16 can also be sensed, enabling the presence and speed of the particles 34 to be monitored. As an example, FIG. 5 represents the effect that a single particle 34 of greater density than the fluid can have on the signal peak gain of the sensing device 10, resulting in loss of resonance during that period of time in which the particle 34 is in transit through the vibrating freestanding portion 16 of the tube 14. A similar decrease in quality factor (Q) of the tube 14 may also occur and be similarly tracked. By measuring the length of this disturbance, the transit time of the particle 34 can be readily ascertained. Alternatively, and as represented in FIG. 6, if the sensing device 10 is operated with feedback so that the drive electrode 22 maintains the freestanding portion 16 at resonance, the shift in frequency necessary to maintain the tube portion 16 at resonance can be correlated to a change in density of the material within the freestanding portion 16, again evidencing the presence of the particles 34 within the freestanding portion 16. In each case, the width of the peak corresponds to the transit time of the particle 34, which in turn is proportional to the speed that the particles 34 are moving through the tube 14. Because wider peaks correspond to greater resistance to movement of the particles 34 through the tube 14 resulting from frictional forces between the particles 34 and walls of the tube passage 20, the peak width an be correlated to the lubricity or viscosity of the fluid.

The efficacy of the technique described above can be appreciated on the basis of the densities of fluids relative to materials that can be used to form the particles 34. In an investigation leading to the invention, various fluids were flowed through silicon and glass tubes formed in accordance with Tadigadapa et al. The measured densities (g/cc) of the different fluid-tube combinations were as follows:

|  | Silicon Tube | Glass Tube |
| --- | --- | --- |
| Coolant/antifreeze | 1.12622 | 1.12598 |
| Water | 0.99904 | 0.99902 |
| Motor Oil (10W40) | 0.87785 | 0.87780 |
| Kerosene | 0.85450 | 0.85435 |
| Diesel Fuel | 0.82258 | 0.82255 |

-continued

|  | Silicon Tube | Glass Tube |
|---|---|---|
| Methanol | 0.79592 | 0.79597 |
| Gasoline | 0.75954 | 0.75940 |

The density of steel is about 7.83 gm/cc and of hard rubber is about 1.95 gm/cc, suggesting that a single spherical particle 34 as small as about one hundred micrometers in diameter can cause a measurable change in the density, and therefore resonant frequency, of the tube 14 for the purpose of sensing and tracking the motion of the particle 34 through the tube 14. In addition to steel and hard ruber, a variety of other materials could be used, particularly iron, nickel, cobalt, titanium and their alloys (including iron-nickel-cobalt alloys such as KOVAR®), stainless steels, low carbon steels, glass, ceramics, and various other materials meet the functional requirements of this invention. Preferred, sizes, densities, and materials for the particles 34 will depend on the size of the tube passage 20 and the sensing technique used, though it is believed that particles 34 with diameters on the order of about 50 to about 100 micrometers are suitable for use in a tube 14 whose passage 20 has cross-sectional dimensions of about 500 by about 200 micrometers.

The configuration and etching of the tube 14 through which the fluid flows can be modified to increase the interaction of the particles 34 with the tube 14 and thereby improve the sensitivity of the device 10. For example, as represented in FIG. 3, the walls of the passage 20 can be corrugated or otherwise made rough during micromachining of the tube 14 to increase particle-wall interactions. If the tube 14 is fabricated by plasma etching, a two-step etch and passivation process often used in micromachining techniques can be adjusted to scallop the sidewalls of the tube 14. Further modifications to the geometry of the passage 20, including obstructions that protrude into the passage 20, can also be incorporated into the design of the tube 14 to increase particle-wall interactions. Alternatively or in addition, the particles 34 can be formed to have rough surfaces or nonspherical shapes to enhance drag on the walls of the tube passage 20 by increasing surface area.

FIG. 3 further represents the use of a magnetic field to promote the interaction of the particles 34 with the walls of the passage 20. In particular, a magnetic field-generating device 44 in the form of a magnet film or coil, electromagnet, or charged plate located externally to the device 10 or integrated onto the device 10 can be used to apply a constant or variable force on particles 34 formed of a ferromagnetic material (such as iron, nickel, steel, etc.) so that, depending on the strength of the force, interaction of the particles 34 with the walls of the passage 20 is promoted and movement of the particles 34 within the passage 20 is slowed or even stopped. In the latter case, one or more particles 34 of adequate size can create a sufficient obstruction to cause a pressure drop or flow rate change in the tube 14 by which viscosity can be measured. Alternatively, by generating a magnetic field strength that slows the particles 34 and pulls them into contact with the walls of the passage 20, the friction of the particles 34 with the passage walls and the resulting effect on particle motion can be used to measure lubricity of the fluid. By applying a variable magnetic field, both a static and kinematic or dynamic coefficient of friction/lubricity can be measured. As another alternative, it is foreseeable that the device 10 could be oriented such that gravity alone is sufficient to pull dense particles 34 into contact with a wall of the passage 20. With each of these approaches, not only does the device 10 function to track the movement of the particles 34, but the device 10 can also function to influence the movement of the particles 34 through the tube 14.

Figure 4:
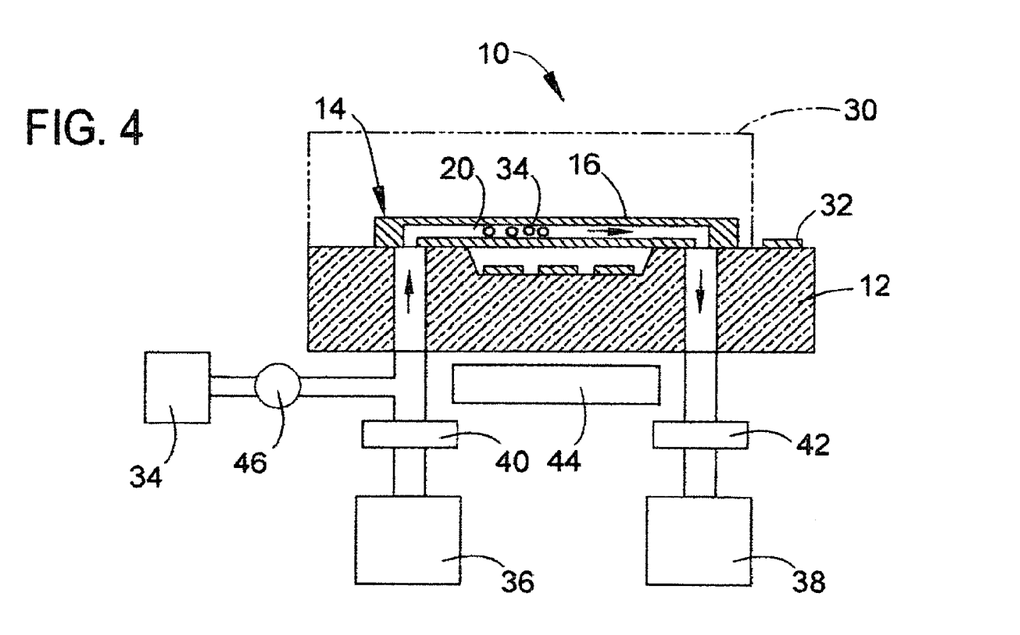
FIG. 4 is a cross-sectional view of the sensing device of FIGS. 1 through 3 in a fluid system that enables bidirectional flow of the fluid through the micromachined tube in accordance with another embodiment of this invention.

The sensing device 10 of FIG. 3 can be adapted for use with a variety of sources for the fluid. For example, the fluid could be introduced into the device 10 with a syringe, syringe pump, pipette, or other type of pump, as can the particles 34 if suspended in the fluid from a second source. Premixed or presorted particles can be added to a fluid sample of known volume and mixed together prior to injection into the device 10. In FIG. 4, the device 10 is shown installed between pairs of pumps 36 and 38 and filters 40 and 42, the latter of which may be magnetic filters or mechanical filters such as simple screens or sieves attached to fittings that connect the pumps 36 and 38 to the device 10. FIG. 4 also shows a magnet 44 placed in proximity to the tube 14 to promote physical interaction between the particles 34 and the walls of the passage 20. With the embodiment of FIG. 4, the particles 34 can be introduced into a closed fluid circuit through a valve 46, and the flow of the fluid can be periodically reversed to move the particles 34 back and forth through the device 10 and its resonating tube 14 under controlled constant or various selected field and temperature conditions. Reversing the movement of the particles 34 from one filter 40/42 to the other 42/40 can be employed to pass the particles 34 through the tube passage 20 any number of times. The field strength of the magnet 44 can be varied while maintaining the fluid at a substantially constant temperature to measure an average transit time for the particles 34 through the passage 20. Alternatively or in addition, the temperature of the fluid can be varied with a suitable heating element (not shown) while maintaining a constant field strength with the magnet 44 to obtain additional particle transit time/speed values indicative of temperature-related changes in lubricity and/or viscosity. When all particles 34 have exited the passage 20 and have been trapped against one of the filters 40 or 42, the density, specific gravity or chemical concentration of the fluid can be measured in accordance with Tadigadapa et al. by continuing the flow of an additional amount of the fluid through the resonating tube 14. In this manner the lubricity, viscosity, and density of the fluid can be measured, as well as the presence of any contaminants by comparing the sensed density to a known density value for the fluid from theoretical or empirical data. As an alternative to the embodiment shown in FIG. 4, it is foreseeable that a circulating fluid circuit could be employed to repeatedly pass the particles 34 through the passage 20.

Figure 7:
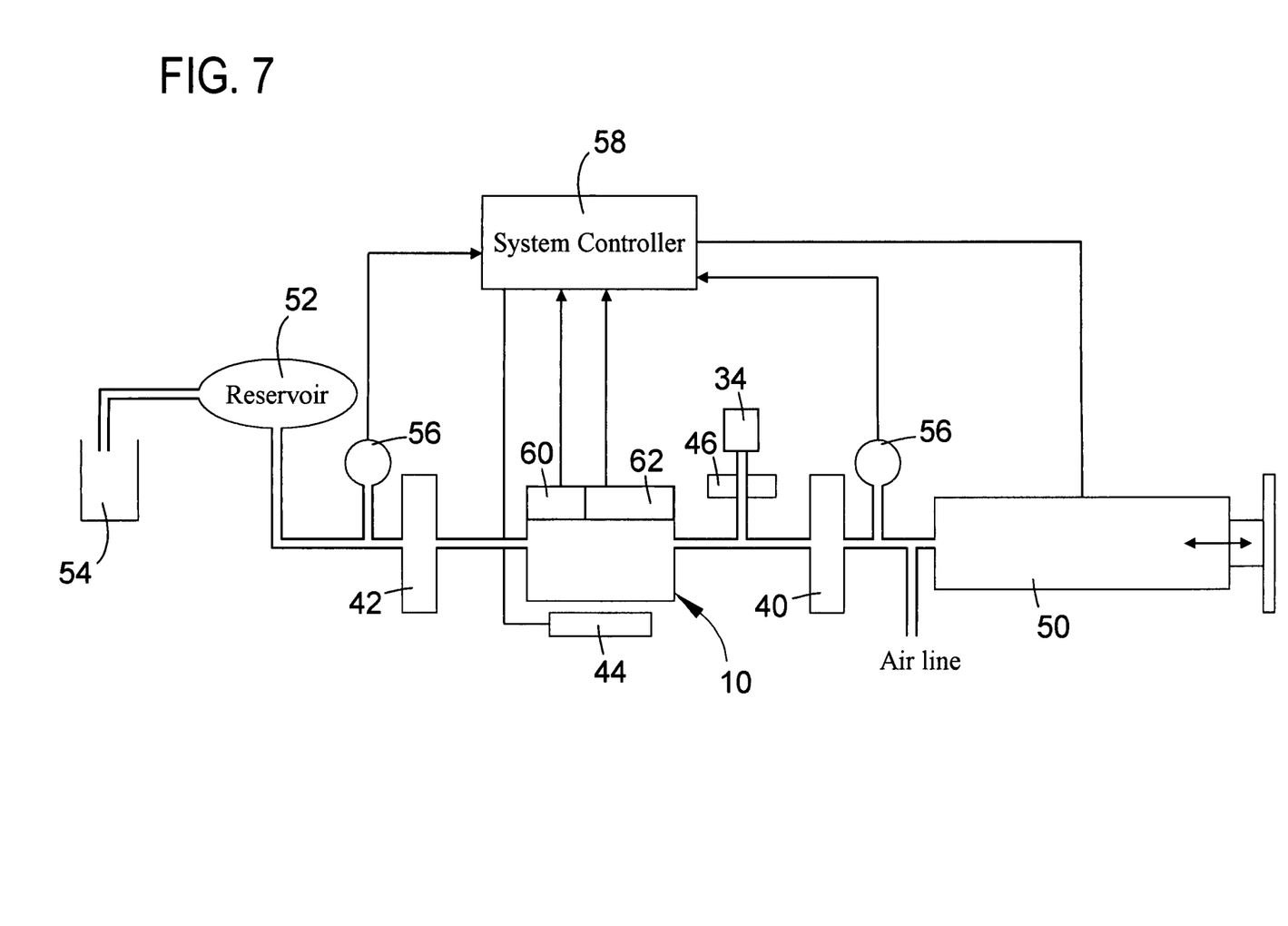
FIG. 7 schematically represents a sensing system that makes use of a sensing device of this invention.

FIG. 7 represents a suitable test system for employing the sensing device 10 of this invention. The source of the fluid is represented as a syringe pump 50, though from the foregoing it is understood that a variety of fluid sources could be used. The system incorporates various components described in reference to FIG. 4, which are identified in FIG. 7 with the same reference numbers. As seen in FIG. 7, the fluid passes through a filter 40 before the introduction of the particles 34 through a valve 46 and subsequent delivery of the particle-containing fluid to the sensing device 10. Downstream of the device 10, the fluid is accumulated in a reservoir 52 after flowing through a second filter 42. In this manner, it is possible to periodically reverse the flow of the fluid through the device 10 between the pump 50 and the reservoir 52. Alternatively or eventually, the fluid can be removed from the system through a drain 54. Pressure sensors 56 are provided by which the pressure drop through the system and accumulation of particles 34 at the filters 40 and 42 can be monitored. The system is also shown equipped with a magnet 44 for the purpose described for the embodiment of FIGS. 3 and 4, namely, to promote interaction of the particles 34 with the walls of the passage 20 to enhance the sensitivity of the device 10 to viscosity and lubricity effects.

Because viscosity is influenced by fluid temperature, the device 10 is shown in FIG. 7 as also being equipped with a thermal control system 60 for sensing and regulating the temperature of the fluid flowing through the tube 14. The fluid temperature will also influence the Young's and shear moduli of the materials from which the tube 14 is fabricated, causing the resonant frequency of the tube 14 to shift. By sensing the temperature of the tube 14, and therefore effectively the fluid within the tube 14, appropriate signal processing with on-chip circuitry 62 can be performed on the output of the device 10 to compensate for these temperature effects. The thermal control system 60 also enables the measurement of fluid properties and particle speed with respect to field strength at different temperatures, as discussed with reference to FIG. 4. The thermal control system 60 can comprise one or more Peltier (thermoelectric) panels, electrical resistance heaters, or other thermal devices. The thermal control system 60 can also include heat sinks and fans to achieve cooling and heating of the fluid within the device 10 to a desired temperature.

Finally, the system of FIG. 7 is shown as including a system controller 58 to monitor and control various components of the system. For example, feedback control of the thermal control system 60 enables the temperature of the fluid to be held at a stable temperature to within a few millidegrees Celsius. The system controller 58 also makes use of feedback from the pressure sensors 56, pump 50, and magnet 44 to enable the operation of the pump 50 and magnet 44 to be regulated with respect to each other and test parameters programmed into the system via the system controller 58. Finally, the system controller 58 can receive the output of the device 10, such as the frequency, amplitude, and phase of the freestanding tube portion 16 sensed by the sensing electrodes 24, to control the drive electrode 22 for the purpose of maintaining the tube 14 at resonance.

Figure 8:
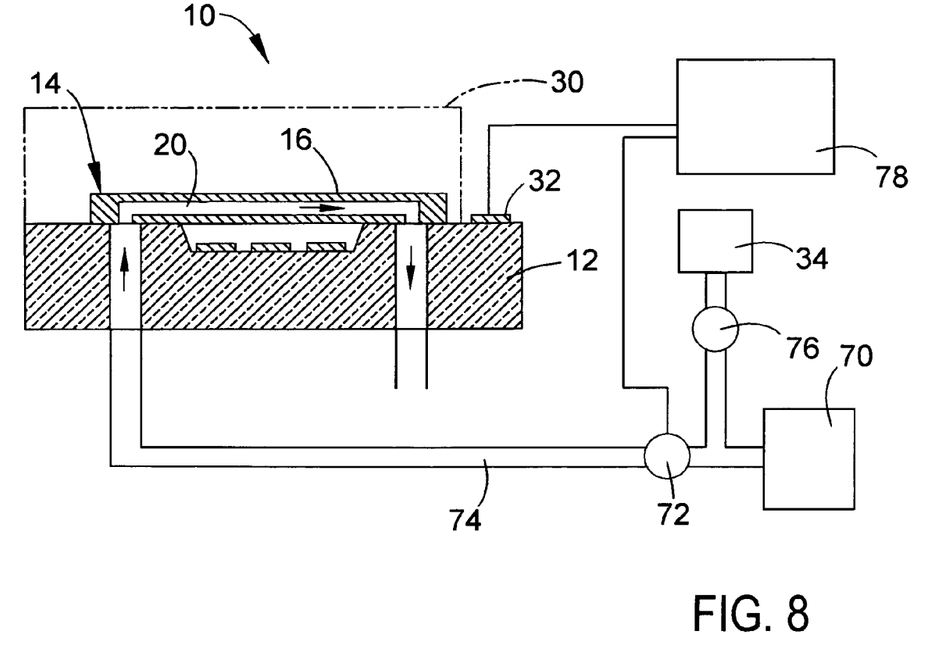
FIG. 8 is a cross-sectional view of the sensing device of FIGS. 1 through 2 in a fluid system that enables time-based sensing of viscosity of the fluid through the micromachined tube in accordance with another embodiment of this invention.
Figure 9:
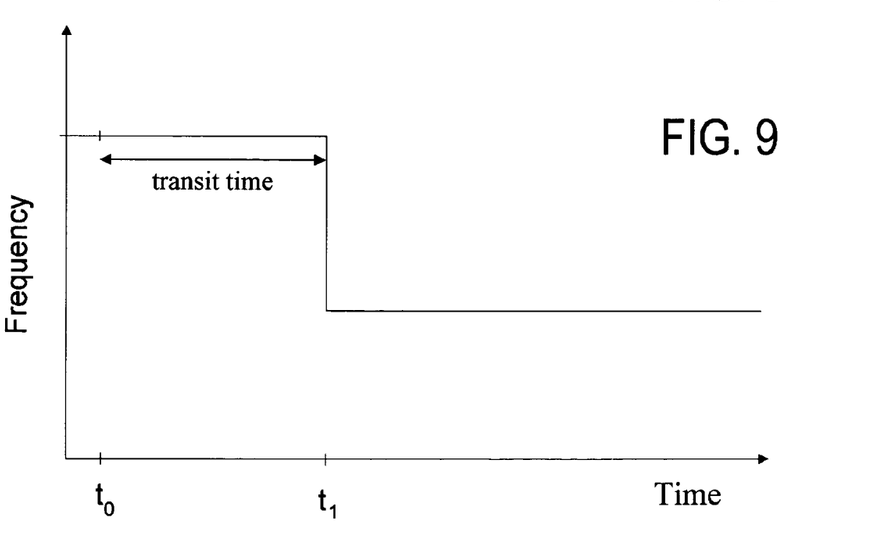
FIG. 9 is a graph representing a mode for sensing the viscosity of the fluid flowing to and then through the sensing device of FIG. 8.

FIG. 8 represents another embodiment of the invention in which the viscosity of the fluid flowing through the device 10 of FIGS. 1 and 2 can be measured without the use of particles 34. Instead of sensing the presence and transit of particles through the tube 14 by sensing the influence that particles would have on the vibration characteristics of the tube 14, FIG. 9 represents a fluid system that enables time-based sensing of viscosity of the fluid flowing through the micromachined tube 14. In particular, the fluid is delivered by a suitable source 70 (e.g., any of those cited for the pumps 36 and 50 of previous embodiments) to a passage 74 through a suitable valve 72. The passage 74 can be formed by a tube separately formed and attached to the device 10 or integrally formed within the substrate 12 of the device 10. The timing of the opening of the valve 72 can be controlled and monitored by a controller 78 that also communicates with the device 10, as represented by an electrical connection to the pad 32 on the device 10. As an optional aspect of this embodiment, particles 34 of the type described previously can be controllably introduced into the fluid within the passage 74 through a second valve 76, such as in the same manner described in reference to FIGS. 4 and 7. As represented in FIG. 9, the viscosity of the fluid can be measured by timing the interval required for the fluid (with or without particles 34) to travel from the valve 72 to the freestanding portion 16, the latter event being sensed by a change in the resonant frequency of the tube 14 (e.g., resulting from the difference in density of the air initially within the tube 14 and the fluid that subsequently enters the tube 14). As in FIG. 7, the temperature of the tube 14 can be sensed and controlled to maintain a constant fluid temperature or vary the temperature of the fluid to more fully characterize the viscosity of the fluid. Using the same tube 14 and device 10 or a separate tube within the same or separate device, the lubricity of the fluid can also be measured to provide a single system capable of measuring the viscosity, density, and lubricity of the fluid.

Figure 10:
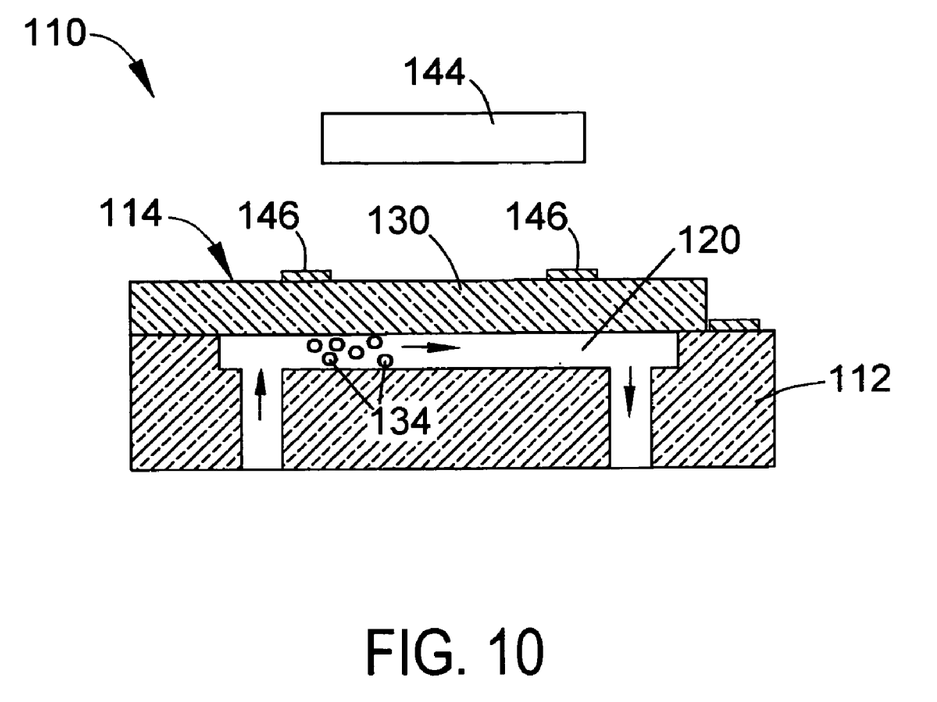
FIG. 10 is a cross-sectional view of a sensing device with a stationary micromachined tube through which a fluid of interest flows in accordance with still another embodiment of this invention.

FIG. 10 represents an embodiment of the invention in which a technique other than a resonance-based approach is used to monitor the motion of one or more particles 134 within a fluid flowing through a micromachined tube 114. Because tracking of the particles 34 is by means other than the resonant frequency of the tube 114, the tube 114 can be stationary during operation of the sensing device 110. As such, the passage 120 of the tube 114 in FIG. 10 can be defined by a trench formed in a silicon, plastic, or glass substrate 112 and a cover 130 bonded to the substrate 112 to enclose the trench. As one example of this embodiment, the particles 134 can be formed of a ferromagnetic material and the presence and movement of the particles 134 through the tube 114 are monitored with a magnetic field generated by a magnet 144. In another approach, the cover 130 is formed of glass or another material that is sufficiently optically translucent or transparent to permit optical monitoring of the particles 34 as they flow through the passage 120, such as with a camera scope 144. Metal runners 146 can be used to magnetically sense the passing of particles 134 formed from a ferromagnetic material. In view of the above, it can be appreciated that, depending on the properties of the particles 134 (e.g., temperature, density, electrical, magnetic, etc.), a variety of techniques can be used to track the particles 134 through the tube 114, including infrared, ultrasonic, electrical, and magnetic sensing techniques. Filters of the type shown in FIGS. 4 and 7 can also be used with this embodiment of the invention to repeatedly flow the same fluid back and forth through the sensing device 110.

As with the device 10 of FIGS. 1 through 7, devices 110 in accordance with FIG. 10 are able to ascertain the viscosity or lubricity of a fluid within the tube 114 by observing the effect that the particles 134 have on the flow of the fluid and/or the time required for the particles to travel through the tube 114 relative to the flow rate of the fluid. As was previously noted with reference to FIG. 3, while multiple particles 134 are represented in FIG. 10, a single particle 134 relatively large in relation to the passage 120 could be used. Also in accordance with the previously-described device 10, the operation of the device 110 is on the basis that interactions between the particles 134 and the fluid impede the flow of the fluid through the tube 114 and can be proportionally correlated to the viscosity of the fluid, and interactions between the particles 134 and the walls of the passage 120 impede the movement of the particles 134 through the tube 114 and can be proportionally correlated to the lubricity of the fluid. Therefore, by using a fixed pressure or flow rate through the tube 114 and sensing and tracking the movement of the particles 134 through the tube 114, the lubricity and/or viscosity of the fluid can be determined. Because the functional intent of the particles 134 is to interact with the fluid and/or the walls of the passage 120 in a manner that enables the viscosity and lubricity of the fluid to be detected, any one or more of the various approaches noted previously for promoting particle-wall interactions can be employed in the embodiment of FIG. 10 to enhance the sensitivity of the device 110.

In view of the above, the devices 10 and 110 of this invention are able to measure the viscosity and/or lubricity of a fluid, as well as detect changes in viscosity and lubricity that may occur over time such as when a lubricant or fuel breaks down or becomes contaminated. In the case of automotive engines, monitoring of the engine oil in this manner can be used to indicate when an oil change is needed, and fuel can be monitored to assess the condition of the fuel and fuel system, including wear of fuel system components such as fuel injectors. Historical data can be saved and compared to real-time data to determine if a lubricant, fuel, or lubrication or fuel system components have degraded or need replacement. Advantageously, the sensing devices 10 and 110 of this invention can be made extremely thin, permitting their installation on an engine as an aftermarket sensor module for truck and automotive applications. By also monitoring the resonant frequency of the tube 14 of the device 10, the density of a fuel or lubricant can also be determined and used to indicate contamination.

While the invention has been described in terms of certain embodiments, it is apparent that other forms could be adopted by one skilled in the art. Therefore, the scope of the invention is to be limited only by the following claims.

The invention claimed is:

1. A method of assessing a rheological property of a fluid, the method comprising the steps of:
   flowing the fluid through a passage within a portion of a tube, the fluid having suspended therein at least one solid particle whereby the at least one solid particle also flows through the passage; and
   assessing a rheological property of the fluid within the tube by tracking movement of the at least one solid particle or tracking movements of the fluid and the at least one solid particle as the fluid flows through the portion, wherein the movement is tracked through the portion relative to the pressure or flow rate of the fluid;
   wherein the portion of the tube comprises a freestanding portion and the method further comprises:
   vibrating the freestanding portion of the tube at or near a resonant frequency thereof; and
   sensing movement of the freestanding portion of the tube.

2. A method according to claim 1, further comprising the step of intentionally introducing the at least one solid particle into the fluid to suspend the at least one solid particle in the fluid and cause the at least one solid particle to flow through the portion of the tube, wherein the assessing step comprises tracking the movement of the at least one solid particle through the portion relative to the flow of the fluid through the portion.

3. A method according to claim 2, wherein the movement of the at least one solid particle through the portion is tracked by a technique chosen from the group consisting of optical, infrared, ultrasonic, electrical, magnetic, and resonance sensing techniques.

4. A method according to claim 3, wherein the at least one solid particle contains a ferromagnetic material and the movement of the at least one solid particle through the portion is tracked and influenced magnetically.

5. A method according to claim 2, wherein the at least one solid particle is one of a plurality of particles introduced into the fluid to flow through the portion.

6. A method according to claim 2, wherein the portion has an internal surface defining the passage therethrough and the internal surface is rough to promote physical interaction with the at least one solid particle.

7. A method of assessing a rheological property of a fluid, the method comprising the steps of:
   flowing the fluid through a passage within a portion of a tube;
   intentionally introducing at least one solid particle into the fluid to suspend the at least one solid particle in the fluid and cause the at least one solid particle to flow through the portion of the tube;
   assessing a rheological property of the fluid within the tube by tracking movement of the at least one solid particle through the portion relative to the flow of the fluid through the portion;
   wherein the at least one solid particle contains a ferromagnetic material and the method further comprises applying a magnetic field to alter the movement of the at least one solid particle through the portion.

8. A method according to claim 7, wherein the method measures the viscosity of the fluid by sensing a pressure drop in the fluid as a result of the at least one solid particle obstructing the flow of the fluid through the portion.

9. A method according to claim 8, wherein the magnetic field is applied to stop the movement of the at least one solid particle through the portion.

10. A method according to claim 7, wherein the magnetic field is applied to pull the at least one solid particle into contact with a wall of the portion of the tube that defines the passage.

11. A method according to claim 10, wherein the method measures the lubricity of the fluid.

12. A method of assessing a rheological property of a fluid, the method comprising the steps of:
   flowing the fluid through a passage within a portion of a tube;
   introducing at least one solid particle into the fluid to suspend the at least one solid particle in the fluid and cause the at least one solid particle to flow through the portion of the tube;
   assessing a rheological property of the fluid within the tube by tracking movement of the at least one solid particle through the portion relative to the flow of the fluid through the portion;
   collecting the at least one solid particle after the at least one solid particle exits a first end of the portion; and then
   reversing the flow of the fluid through the portion and collecting the at least one solid particle after the at least one solid particle exits an oppositely-disposed second end of the portion.

13. A method according to claim 2, further comprising maintaining the portion and the fluid therein at a substantially constant temperature while the at least one solid particle moves through the portion.

14. A method of assessing a rheological property of a fluid, the method comprising the steps of:
   flowing the fluid through a passage within a portion of a tube, the fluid optionally having suspended therein at least one solid particle whereby, if suspended in the fluid, the at least one solid particle also flows through the passage; and
   assessing a rheological property of the fluid within the tube by tracking movement of the at least one solid particle if suspended in the fluid, or tracking movements of the fluid and the at least one solid particle if suspended in the fluid, as the fluid flows through the portion;
   wherein the tube is a component of a fluid system, the fluid is a lubricant or fuel, and the viscosity or lubricity, the mass flow rate, the density, and the temperature of the fluid are used to indicate the condition of the fluid and the fluid system.

15. A method of assessing a rheological property of a fluid, the method comprising the steps of:

flowing the fluid through a passage within a portion of a tube, the fluid optionally having suspended therein at least one solid particle whereby, if suspended in the fluid, the at least one solid particle also flows through the passage; and assessing a rheological property of the fluid within the tube by tracking movement of the at least one solid particle if suspended in the fluid, or tracking movements of the fluid and the at least one solid particle if suspended in the fluid, as the fluid flows through the portion;

wherein the portion of the tube comprises a freestanding portion, the method further comprising the steps of:

vibrating the freestanding portion of the tube at or near a resonant frequency thereof; and sensing movement of the freestanding portion of the tube;

wherein the movement of the at least one solid particle through the freestanding portion is tracked by monitoring changes in at least one of the signal peak gain and resonant frequency of the freestanding portion relative to time.

16. A method according to claim 15, wherein the at least one solid particle is not suspended in the fluid flowing through the passage, and the movement of the fluid through the freestanding portion is tracked by monitoring changes in at least one of the signal peak gain and resonant frequency of the freestanding portion relative to time.

17. A method according to claim 15, wherein the at least one solid particle is suspended in the fluid flowing through the passage, the at least one solid particle has a different density than the density of the fluid, and the movement of the at least one solid particle through the freestanding portion is tracked by monitoring changes in at least one of the signal peak gain and resonant frequency of the freestanding portion relative to time.

18. A method according to claim 15, further comprising determining the mass flow rate of the fluid flowing through the tube by sensing a Coriolis force-induced twisting of the freestanding portion of the tube.

19. A method according to claim 15, further comprising determining at least one of the viscosity, lubricity, and density of the fluid flowing through the tube by sensing changes in the resonant frequency of the freestanding portion of the tube relative to time.

20. A method according to claim 15, further comprising the step of micromachining the freestanding portion of the tube to be a cantilevered portion of the tube above a surface of a substrate supporting the tube.

21. A sensing device for assessing a rheological property of a fluid, the device comprising:

a substrate;

a tube supported by the substrate and comprising a fluid inlet, a fluid outlet, and a portion between the fluid inlet and the fluid outlet so as to define a continuous passage through the tube;

a fluid flowing through the continuous passage within the tube, the fluid optionally having suspended therein at least one solid particle whereby, if suspended in the fluid, the at least one solid particle also flows through the passage;

means for assessing a rheological property of the fluid within the tube by tracking movement of at least one of the fluid and the at least one solid particle through the portion relative to the pressure or flow rate of the fluid;

means for assessing a rheological property of the fluid within the tube by tracking movement of the fluid, or tracking movement of the at least one solid particle if suspended in the fluid, or tracking movements of the fluid and the at least one solid particle if suspended in the fluid, as the fluid flows through the portion, wherein the assessing means tracks the movement through the portion relative to the pressure or flow rate of the fluid.

* * * * *